United States Patent [19]

Bull et al.

[11] Patent Number: 5,278,061

[45] Date of Patent: Jan. 11, 1994

[54] AFFINITY CHROMATOGRAPHY MATRIX USEFUL IN PURIFYING INTERLEUKIN-1β CONVERTING ENZYME

[75] Inventors: Herb G. Bull, Westfield; Kevin T. Chapman, Scotch Plains, both of N.J.

[73] Assignee: Merck & Co., Inc., Rahway, N.J.

[21] Appl. No.: 746,685

[22] Filed: Aug. 16, 1991

[51] Int. Cl.$^5$ ............................ C12N 9/48; A23J 1/00
[52] U.S. Cl. .................................... 435/212; 435/195; 435/814; 435/815; 530/412; 530/413
[58] Field of Search ............... 435/195, 212, 814, 815; 530/412, 413

[56] References Cited

PUBLICATIONS

Sleath et al. J. Biol. Chem. vol. 265 No. 24 (Aug. 1990) 14526–14528.
Bull et al. J. Biol. Chem. vol. 260 No. 5 (Mar. 1985) pp. 2963–2972.
Black, et al J. Biol. Chem. 263, 9437–9442 (1988).
Black, et al J. Biol. Chem. 264, 5323–5326 (1989).
Black, et al FEB Lett. 247, 286–290 (1989).
Kostura, et al Proc. Natl. Acad. Sci. 86, 5227–5231 (1989).

Primary Examiner—Merrell C. Cashion, Jr.
Assistant Examiner—Bennett Celsa
Attorney, Agent, or Firm—Curtis C. Panzer; Joseph F. DiPrima; Hesna J. Pfeiffer

[57] ABSTRACT

Affinity chromatography matrices are disclosed which are useful in purifying interleukin-1β converting enzyme (ICE) from crude or partially purified cell lysate preparations. The chromatographic matrices comprise a specific ICE inhibitor of Formula I which is attached to an affinity column support by means of a bifunctional spacer.

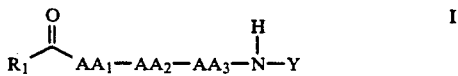

2 Claims, No Drawings

AFFINITY CHROMATOGRAPHY MATRIX USEFUL IN PURIFYING INTERLEUKIN-1β CONVERTING ENZYME

BACKGROUND OF THE INVENTION

This invention relates to affinity chromatography. More particularly, the invention concerns the use of affinity chromatography matrices comprising a support, a bifunctional spacer and a compound (ligand) having a high and specific affinity for the compound sought to be isolated and/or purified. Even more particular, the invention relates to affinity chromatography matrices useful for purifying active interleukin-1β converting enzymes (ICE).

The literature is replete with articles, monographs, and books on the subject of affinity chromatography, including such topics as affinity chromatography supports, crosslinking members, ligands and their preparation and use. A sampling of those references includes:

Affinity chromatography: general methods. *Methods Enzymol.* 1990, 182 (Guide Protein Purif.), 357–71;
Novel affinity-based processes for protein purification. *J. Ferment. Bioeng.* 1990, 70(3), 199–209;
Applications of preparative high-performance liquid chromatography to the separation and purification of peptides and proteins. *J. Chromatogr.* 1989, 492, 431–69;
Large-scale purification of enzymes. *Appl. Microbiol. Res., Ciba Found. Symp.* 1985, 111(Enzymes Org. Synth.), 40–56 (Eng).;
Purification of enzymes by heparin-Sepharose affinity chromatography. *J. Chromatogr.* 1980, 184(3), 335–45;
Principles of multi-enzyme purification by affinity chromatography. *Enzyme Eng.* 1978, 4, 441–2;
Purification of enzymes and other biologically active proteins by chromatography on low-molecular-weight substances immobilized on solid supports. *Postepy Biochem.* 1977, 23(1), 113 27;
General ligand affinity chromatography in enzyme purification. Ligands, affinity chromatography, enzyme purification. *J. Macromol. Sci., Chem.* 1976, A10(1-2), 15–52;
Affinity purification of enzymes. *Chem. Technol.* 1975, 5(9), 564–71;
Chromatography, affinity. *Encycl. Polym. Sci. Eng.* 1985, 3, 531–48;
Bioaffinity chromatography. *Pract. High Perform. Liq. Chromatogr.* 1976, 193–206;
Affinity chromatography of plasma proteins—an overview. Proc. Int. Workshop Technol. Protein Sep. Improv. Blood Plasma Fractionation, 1977, 422-35;
Affinity chromatography of enzymes. *Affinity Chromatogr., Proc. Int. Symp.* 1977 (Pub. 1978), 25–38;
Protein immobilization and affinity chromatography. *Biotechnol. Appl. Proteins Enzymes. Pap. Conf.* 1976 (Pub. 1977), 83–102;
Use of affinity chromatography in protein structure studies. *Pept., Proc. Eur. Pept. Symp.,* 11th 1971 (Pub. 1973), 203–22;
Affinity chromatography of enzymes. *Fed. Eur. Biochem. Soc. Meet., [Proc]* 1974, 30;
Support materials for immobilized enzymes and affinity chromatography. *Bonded Stationary Phases Chromatogr.* 1974, 93–112;
Supports for immobilized enzymes and affinity chromatography. *Chem. Technol.* 1974, 4(11), 694–700;
Affinity chromatography. Enzyme-inhibitor systems. *Methodol. Develop Biochem.* 1973, 2, 109–12;
Affinity chromatography. Specific separation of proteins. *Chromatographia* 1971, 4(12), 578–87;
Affinity chromatography. A Practical approach, IRL Press Limited, Oxford England (1985); and
Methods in Enzymology, Vol. 34: Affinity Techniques. Enzyme Purification: 1974. 810 pp.

A wide variety of affinity chromatography supports (with and without spacers) and support/ligands (with and without spacers) are disclosed in the SIGMA catalog, SIGMA CHEMICAL Co., St. Louis, Mo.

Interleukin-1β converting enzyme (ICE) has been identified as the enzyme responsible for converting precursor interleukin-1β (IL-1β) to biologically active IL-1β. Accordingly, interleukin-1β converting enzyme is useful in the diagnosis of IL-1 mediated diseases or in enhancing the production of IL-1.

Mammalian interleukin-1 (IL-1) is an immunoregulatory protein secreted by cell types as part of the inflammatory response. The primary cell type responsible for IL-1 production is the peripheral blood monocyte. Other cell types have also been described as releasing or containing IL-1 or IL-1 like molecules. These include epithelial cells (Luger, et al., J. Immunol. 127: 1493–1498 (1981), Le et al., J. Immunol. 138: 2520–2526 (1987) and Lovett and Larsen, J. Clin. Invest. 82: 115–122 (1988), connective tissue cells (Ollivierre et al., Biochem. Biophys. Res. Comm. 141: 904–911 (1986), Le et al, J. Immunol. 138: 2520–2526 (1987), cells of neuronal origin (Giulian et al., J. Esp. Med. 164: 594–604 (1986) and leukocytes (Pistoia et al., J. Immunol. 136: 1688–1692 (1986), Acres et al., Mol. Immuno. 24: 479–485 (1987), Acres et al., J. Immunol. 138: 2132–2136 (1987) and Lindenmann et al., J. Immunol 140: 837–839 (1988).

Biologically active IL-1 exists in two distinct forms, IL-1α with an isoelectric point of about pI 5.2 and IL-1β with an isoelectric point of about 7.0 with both forms having a molecular mass of about 17,500 (Bayne et al., J. Esp. Med. 163: 1267–1280 (1986) and Schmidt, J. Esp. Med. 160: 772 (1984). The polypeptides appear evolutionarily conserved, showing about 27–33% homology at the amino acid level (Clark et al., Nucleic Acids Res. 14: 7897–7914 (1986).

Mammalian IL-1β is synthesized as a cell associated precursor polypeptide with a molecular mass of about 31.4 kDa (Limjuco et al., Proc. Natl. Acad. Sci USA 83: 3972–3976 (1986). Precursor IL-1β is unable to bind to IL-1 receptors and is biologically inactive (Mosley et al., J. Biol. Chem. 262: 2941–2944 (1987). Biological activity appears dependent upon some form of proteolytic processing which results in the conversion of the precursor 31.5 kDa form to the mature 17.5 kDa form. Evidence is growing that by inhibiting the conversion of precursor IL-1β to mature IL-1β, one can effectively inhibit the activity of interleukin-1.

Mammalian cells capable of producing IL-1β include, but are not limited to, karatinocytes, endothelial cells, mesangial cells, thymic epithelial cells, dermal fibroblasts, chondrocytes, astrocytes, glioma cells, mononuclear phagocytes, granulocytes, T and B lymphocytes and NK cells.

As discussed by J. J. Oppenheim, et al. Immunology Today, vol. 7(2): 45–56 (1986), the activities of interleukin-1 are many. It has been observed that catabolin, a factor that promotes degradation of cartilage matrix, also exhibited the thymocyte comitogenic activities of IL-1 and stimulates chondrocytes to release collagenase neutral proteases and plasminogen activator. In addition, a plasma factor termed proteolysis inducing factor stimulates muscle cells to produce prostaglandins which in turn leads to proteolysis, the release of amino acids and, in the long run, muscle wasting, and appears to represent a fragment of IL-1 with fever-inducing, acute phase response and thymocyte co-mitogenic activities.

IL-1 has multiple effects on cells involved in inflammation and wound healing. Subcutaneous injection of IL-1 leads to margination of neutrophils and maximal extravascular infiltration of the polymorphonuclear leukocytes (PMN). In vitro studies reveal IL-1 to be a chemotactic attractant for PMN to activate PMN to metabolize glucose more rapidly to reduce nitroblue tetrazolium and to release their lysozomal enzymes. Endothelial cells are stimulated to proliferate by IL-1 to produce thromboxane, to become more adhesive and to release procoagulant activity. IL-1 also enhances collagen type IV production by epidermal cells, induces osteoblast proliferation and alkaline phosphatase production and stimulates osteoclasts to resorb bone. Even macrophages have been reported to be chemotactically attracted to IL-1 to produce prostaglandins in response to IL-1 and to exhibit a more prolonged and active tumoricidal state.

IL-1 is also a potent bone resorptive agent capable upon infusion into mice of causing hypercaleemia and increase in bone resorptive surface as revealed by histomorphometry Sabatini, M. et al., PNAS 85: 5235-5239, 1988.

Accordingly, IL-1 has been implicated in infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. IL-1 has also been implicated in the treatment of bone and cartilage resorption as well as diseases resulting in excessive deposition of extracellular matrix. Such diseases include periodonate diseases interstitial pulmonary fibrosis, cirrhosis, systemic sclerosis, and keloid formation.

SUMMARY OF THE INVENTION

Affinity chromatography matrices are disclosed which are useful in purifying interleukin-1β converting enzyme (ICE) from crude or partially purified cell lysate preparations. The chromatographic matrices comprise a specific ICE inhibitor of Formula I which is attached to an affinity column support by means of a bifunctional spacer.

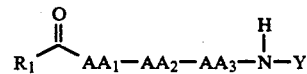

DETAILED DESCRIPTION OF THE INVENTION

In one embodiment the invention encompasses affinity chromatography matrices comprising
(a) a compound of Formula I

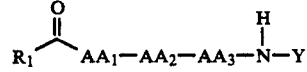

wherein Y is:

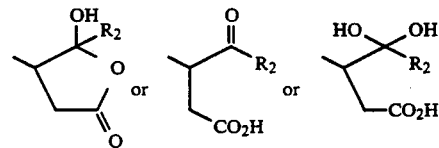

(b) an affinity chromatographic support; and
(c) a spacer co-valently bound to said compound of Formula I and to said support;
said compounds of Formula I defined as those wherein:
$R_1$ is
(a) substituted $C_{1-12}$ alkyl, wherein the substituent is selected from
(1) hydrogen,
(2) hydroxy,
(3) halo,
(4) $C_{1-6}$alkylcarbonyl,
(5) formyl,
(6) amino,
(7) carboxy,
(8) thiol, and
(9) oxiranyl;
(b) aryl $C_{1-6}$ alkyl wherein the aryl group is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl, and
(20) oxazolyl,
and mono and di-substituted aryl as defined above in items (1) to (20) wherein the substitutents are independently $C_{1-6}$alkyl, halo, hydroxy, amino $C_{1-6}$alkyl, thio C$_{1-6}$alkyl, formyl C$_{1-6}$alkyl, and hydroxy C$_{1-6}$alkyl;

R$_2$ is
(a) H, (b) 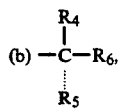

wherein R$_4$ and R$_5$ are each individually selected from hydrogen, fluorine and hydroxy;
R$_6$ is selected from the group consisting of
(1) hydrogen,
(2) fluorine,
(3) substituted C$_{1-6}$ alkyl wherein the substituent is selected from
  (a) hydrogen,
  (b) hydroxy,
  (c) halo,
  (d) C$_{1-6}$ alkylcarbonyl,
(4) aryl C$_{1-6}$ alkyl,
wherein the alkyl is substituted with hydrogen, oxo, C$_{1-3}$ alkyl, halo or hydroxy, wherein aryl is defined as immediately above, and wherein the aryl may be mono and di-substituted, the substituents being each independently C$_{1-6}$alkyl, halo, hydroxy, C$_{1-6}$alkyl amino, C$_{1-6}$alkoxy, C$_{1-6}$alkylthio, and C$_{1-6}$alkylcarbonyl;
(5) C$_{1-6}$ alkyl amino carbonyl C$_{1-6}$ alkyl or C$_{1-6}$ alkyl carbonyl amino C$_{1-6}$ alkyl,
(6) aryl amino carbonyl C1-6 alkyl or aryl carbonyl amino C1-6 alkyl,
wherein aryl is defined as immediately above, and wherein the aryl may be mono and di-substituted, the substituents being each indepentently C$_{1-6}$alkyl, halo, hydroxy, C$_{1-6}$alkyl amino, C$_{1-6}$alkoxy, C$_{1-6}$alkylthio, and C$_{1-6}$alkylcarbonyl;
(7) aryl C$_{1-6}$ alkyl amino carbonyl C$_{1-6}$ alkyl or aryl C$_{1-6}$ alkyl carbonyl amino C$_{1-6}$ alkyl,
wherein aryl is defined as immediately above, and wherein the aryl may be mono and di-substituted, the substituents being each independently C$_{1-6}$alkyl, halo, hydroxy, C$_{1-6}$alkyl amino, C$_{1-6}$alkoxy, C$_{1-6}$alkylthio, and C$_{1-6}$alkylcarbonyl;
AA$_1$ is independently selected from the group consisting of
(a) a single bond, and
(b) an amino acid of formula AI

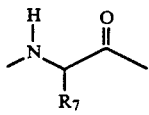

wherein R$_7$ is selected from the group consisting of:
(a) hydrogen,
(b) substituted C$_{1-10}$ alkyl, wherein the substituent is selected from
  (1) hydrogen,
  (2) hydroxy,
  (3) halo,
  (4) —S—C$_{1-4}$ alkyl,
  (5) —SH,
  (6) formyl,
  (7) amino,
  (8) oxiranyl, (9) C$_{1-6}$ alkylcarbonyl,
(10) carboxy,

(11) 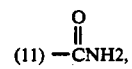

(12) amino carbonyl amino,
(13) C$_{1-4}$ alkylamino, wherein the alkyl moiety is substituted with hydrogen or hydroxy, and the amino is substituted with hydrogen or CBZ,
(14) guanidino, and
(c) aryl C$_{1-6}$ alkyl,
wherein aryl is defined as immediately above, and wherein the aryl may be mono and di-substituted, the substituents being each independently C$_{1-6}$alkyl, halo, hydroxy, amino, thiol, carboxy, formyl, oxiranyl amino C$_{1-6}$alkyl, formyl C$_{1-6}$alkyl, oxiranyl C$_{1-6}$alkyl, thiol C$_{1-6}$alkyl, carboxy C$_{1-6}$alkyl, hydroxy C$_{1-6}$alkyl, and halo C$_{1-6}$alkyl.
AA$_2$ is independently selected from the group consisting of
(a) a single bond, and
(b) an amino acid of formula AII

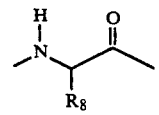

AA$_3$, which are each independently selected from the group consisting of
(a) a single bond, and
(b) an amino acid of formula AIII

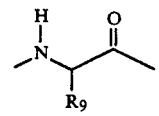

wherein R$_8$ and R$_9$ are each independently selected from the group consisting of
(a) hydrogen,
(b) substituted C$_{1-10}$ alkyl, wherein the substituent is selected from
  (1) hydrogen,
  (2) hydroxy,
  (3) halo,
  (4) —S—C$_{1-4}$ alkyl,
  (5) —SH,
  (6) C$_{1-6}$ alkylcarbonyl,
  (7) carboxy, (8) 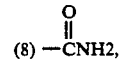

(9) amino carbonyl amino,
(10) C$_{1-4}$ alkylamino, wherein the alkyl moiety is substituted with hydrogen or hydroxy, and the amino is substituted with hydrogen or CBZ,
(11) guanidino,
(12) formyl,
(13) oxiranyl, and
(14) amino,
(c) aryl C$_{1-6}$ alkyl, wherein aryl is defined as immediately above, and wherein the aryl may be mono and di-substituted, the substituents being each independently $C_{1-6}$ alkyl, hydroxy, amino, formyl, thiol, oxiranyl, carboxy, amino $C_{1-6}$ alkyl, formyl $C_{1-6}$ alkyl, oxiranyl $C_{1-6}$ alkyl, thiol $C_{1-6}$ alkyl, carboxy $C_{1-6}$ alkyl, hydroxy $C_{1-6}$ alkyl, and halo $C_{1-6}$ alkyl;

said spacer defined as
(1) a single bond, or
(2) —X—Z—Y—
wherein X and Y are a first and a second reactive or activatable functional group, and X and Y are each independently selected from such moeities as hydroxy, amino, thiol, carboxy, oxiranyl, formyl, halo, isocyanato, and chloro sulphonyl; and Z is selected from such groups as
(a) $C_{1-12}$ alkyl,
(b) aryl
(c) $C_{1-6}$ alkyl aryl,
(d) $C_{1-6}$ alkyl aryl $C_{1-6}$ alkyl,
wherein 1, 2 or more of the carbon atoms of the alkyl may be replaced by an oxygen, sulfur or nitrogen, and wherein aryl includes but is not limited to phenyl, naphthyl, pyridyl or thienyl; and
(e) a peptide of 2 to 10 amino acids, said amino acids included, but not limited to the L- and D-forms of the amino acids including glycine, alanine, valine, leucine, isoleucine, serine, threonine, aspartic acid, asparagine, glutamic acid, glutamine, lysine, hydroxy-lysine, histidine, arginine, phenylalanine, tyrosine, tryptophan, cysteine, methionine, ornithine, β-alanine, homoserine, homotyrosine, homophenylalanine and citrulline.

Such spacers may include, but are not limited to p-benzoquinone, bis-(diazobenzidine), 3,6-bis-(mercurimethyl) dioxane, bisoxiranes, cyanuric chloride, p,p'-difluoro-m,m'-, dicyclohexylcarbodiimide, dinitrophenylsulphone, dimethyladipimidate, dimethylsuberimidate, divinylsulphone, N,N'-ethylene-bis-(iodoacetamide), glutaraldehye, hexamethylene bis-(male-imide), hexamethylene diisocyanate, N,N'-1,3-phenylene-bis-(maleimide), phenol-2,4-disulphonyl chloride, tetra-azotised o-dianisidine, toluene diisocyanate, Woodward's K reagent, water soluble carbodiimides, 6-aminohexanoic acid, hexamethylenedi-amine, 1,7-diamino-4-aza-heptane (3,3'-diamino-dipropylamine), and aminoacids or peptides;

Said affinity chromatography supports may include but are not limited to glass, agarose, polyacrylamine, dextran, including crosslinked dextran (SEPHAROSE), cellulose, and substituted cellulose such as MATREX CELLUFINE FORMYL (AMICON) carboxymethylcellulose and cellulose carbonate, alumina, hydroxyalkylmethacrylate, said support bearing a reactive function such as hydroxyl, carboxyl, amine, phenol, anhydride, aldehyde, epoxide or thiol wherein one functional group of the spacer is condensed with said reactive function on said media, and said second reactive function on the spacer is condensed with said compound of Formula I.

As mentioned in the background portion of this application, such supports and spacers are well known in the art, as are the methods by which a ligand and support are attached to the spacer. See, for example, Affinity Chromatography, A Practical Approach, IRL Press, Ltd., Oxford England (1985), which is hereby incorporated by reference.

Within the first embodiment is the genus wherein the affinity chromatography support is selected from the group consisting of bis-oxirane substituted cellulose such as MATREX CELLUFINE FORMYL or cross-linked dextran, such as SEPHAROSE CL-4B.

One class of this genus is the compounds of Formula I wherein:
$R_1$ is
(a) substituted $C_{1-6}$ alkyl, wherein the substituent is selected from
(1) hydrogen,
(2) hydroxy,
(3) chloro or fluoro, and
(b) aryl $C_{1-6}$ alkyl wherein the aryl group is selected from the group consisting of
(1) phenyl,
(2) naphthyl,
(3) pyridyl,
(4) furyl,
(5) thienyl,
(6) thiazolyl,
(7) isothiazolyl,
(8) benzofuryl,
(9) benzothienyl,
(10) indolyl,
(11) isooxazolyl, and
(12) oxazolyl,
and mono and di-substituted $C_{6-10}$ aryl as defined above in items (1) to (12) wherein the substitutents are independently $C_{1-4}$ alkyl, halo, and hydroxy;

$R_2$ is hydrogen, $AA_1$ is independently selected from the group consisting of
(a) a single bond, and
(b) an amino acid of formula AI

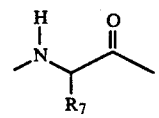

wherein $R_7$ is aryl $C_{1-6}$ alkyl wherein aryl is defined as immediately above, and wherein the aryl may be mono and di-substituted, the substituents being each independently $C_{1-6}$ alkyl, halo, hydroxy, amino $C_{1-6}$ alkyl, Hydroxy $C_{1-6}$ alkyl, thio $C_{1-6}$ alkyl, and formyl $C_{1-6}$ alkyl;

$AA_2$ is independently selected from the group consisting of
(a) a single bond, and
(b) an amino acid of formula AII

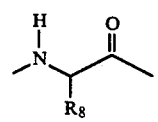

$AA_3$, which are each independently selected from the group consisting of
(a) a single bond, and
(b) an amino acid of formula AIII

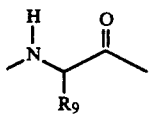

wherein R8 and R9 are each independently selected from the group consisting of
(a) hydrogen,
(b) substituted C1-10 alkyl, wherein the substituent is selected from
  (1) hydrogen,
  (2) hydroxy,
  (3) halo,
  (4) —SH,
  (6) C1-6 alkylcarbonyl,
  (7) carboxy,
  (8) formyl,
  (9) oxiranyl,
  (10) amino,
(c) aryl C1-6 alkyl,
wherein aryl is defined as immediately above, and wherein the aryl may be mono and di-substituted, the substituents being each independently C1-6alkyl, hydroxy, amino, formyl, thiol, oxiranyl, carboxy, amino C1-6 alkyl, formyl C1-6 alkyl, oxiranyl C1-6 alkyl, thiol C1-6 alkyl, carboxy C1-6 alkyl, hydroxy C1-6 alkyl, and halo C1-6 alkyl.

Within this class are the compounds wherein AA1, AA2 and AA3, are each independently selected from the group consisting of the L- and D- forms of the amino acids including glycine, alanine, valine, leucine, isoleucine, serine, threonine, aspartic acid, asparagine, glutamic acid, glutamine, lysine, hydroxy-lysine, histidine, arginine, phenylalanine, tyrosine, tryptophan, cysteine, methionine, ornithine, β-alanine, homoserine, homotyrosine, homophenylalanine and citrulline.

Alternatively, within this class are the subclass of compounds wherein
R1 is C1-3alkyl;
R2 is hydrogen, and
R8 and R9 are each individually
  (a) hydrogen,
  (b) C1-6alkyl,
  (c) mercapto C1-10alkyl,
  (d) hydroxy C1-10alkyl,
  (e) carboxy C1-10alkyl,
  (f) amino C1-10alkyl,
  (g) formyl C1-10alkyl,
  (h) oxiranyl C1-10alkyl,
  (i) aryl C1-6alkyl, wherein the aryl group is selected from phenyl and indolyl, and the aryl group may be substituted with hydroxy, C1-3 alkyl, amino, carboxy, formyl, oxiranyl, thiol, hydroxy C1-6 alkyl, amino C1-6 alkyl, carboxy C1-6 alkyl, formyl C1-6 alkyl, oxiranyl C1-6 alkyl, thiol C1-6 alkyl, halo C1-6 alkyl.

Within this sub-class are the compounds wherein:
R1 is methyl;
R2 is hydrogen;
R8 is C1-6alkyl; and
R9 is substituted C1-10 alkyl
wherein the substituent is
  (a) H,
  (b) OH,
  (c) CO2H,
  (d) NH2,
  (e) formyl,
  (f) oxiranyl,
  (g) halo,
  (h) thiol,
  (i) substituted phenyl C1-6alkyl, wherein the substituent is hydroxy, amino, or carboxy, formyl, oxiranyl, thiol, hydroxy C1-6 alkyl, amino C1-6 alkyl, carboxy C1-6 alkyl, formyl C1-6 alkyl, oxiranyl C1-6 alkyl, thiol C1-6 alkyl, halo C1-6 alkyl.

Exemplifying the invention are the following compounds:
(a) N-(N-Acetyl-tyrosinyl-valinyl-lysinyl)-3-amino-4-oxobutanoic acid;
or a ring chain tautomer or hydrate thereof.

For purposes of this specification the above description for the compounds which explicitly correspond to the following equilibrium form of Y

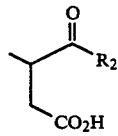

are intended to include the following equilibrium forms as well:

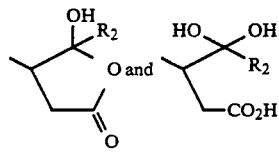

In a second embodiment, the invention also concerns a method of using the above described affinity chromatography matrix for purifying interleukin-1β converting enzyme comprising in sequential order
(a) loading a preparation containing interleukin-1β converting enzyme onto said matrix,
(b) washing said matrix with a buffer having neutral pH (e.g. pH 6.5 to 7.5) to remove contaminating proteins
(c) eluting said interleukin-1β converting enzyme by addition of a compound of Formula I, and
(d) recovering said interleukin-1β converting enzyme.

In affinity chromatography, the affinity matrix is used to selectively extract the enzyme from crude solutions, either as a batch or continuous process. After washing away the contaminating proteins, the enzyme is freed from the matrix by introducing free ligand, which competes with the matrix for binding to the enzyme. The eluted enzyme is freed of inhibitor by dialysis or ultrafiltration techniques, or in the case of potent inhibitors by chemical processes that interfere with binding to the inhibitor.

The affinity matrix is typically packed in a cylindrical column to permit a continuous flow process, although batch operation would be a reasonable alternative for extracting the enzyme from crude preparations. The affinity column is protected by a guard column of native supporting matrix (e.g. Sepharose CL-4B) to filter out proteins that bind non specifically to the matrix and would be difficult to wash away completely from the bound enzyme.

Both columns are typically equilibrated with a buffer at neutral pH prior to application of the enzyme solution, for which 3 or more column volumes is regarded as sufficient. Any nonreactive compound with a pKa near neutrality is satisfactory. We have found N-[2-hydroxyethyl]piperazineN'-[2-ethanesulfonic acid] (HEPES) to be satisfactory, and we include 10% sucrose and 0.1% 3-[3-cholamidopropyl)dimethylammonio]-1-propanesulfonate (CHAPS), because we have found the sucrose and detergent slow the rate of dissociation of the enzyme to inactive monomers.

A consideration somewhat unique to the class of inhibitors represented by Formula I is that their rate constants for association and dissociation from the enzyme are slower than normal. The slow rate constant for association requires that unusually slow flow rates (i.e. less than 1 bed volume per hour) be used in applying the enzyme in order to achieve good retention. A flow rate equivalent to ¼ bed volume per hour has been found reasonable at 4° C.

The bound enzyme is washed with buffer to remove the last traces of contaminating proteins. Extensive washing, using as much as 20 column volumes of buffer, is desirable and leads to no detectable loss during this process. Purifications as high as 1,000 to 100,000 fold are required to achieve pure enzyme, so that even minor contamination is unacceptable.

After washing, the enzyme is eluted from the matrix by including the free ligand, or another inhibitor from the family represented by Formula 1, in the wash buffer. Again, the slow rate constants for equilibration with this class of inhibitors require special consideration. The halflife for dissociation of Compound B, considered to be a model for Compound A when coupled through lysine to the affinity matrix, is ~100 min at 23° C., too slow to use continuous flow to elute the enzyme. Consequently, elution is accomplished in a batch process, in which the column is flooded with free ligand (100 uM has been found to be satisfactory), and then incubated overnight to allow the exchange to reach equilibrium before restarting the flow to elute the enzyme.

Lastly, purified ICE must be separated from the E-I complex. At this point, the purified enzyme is complexed with the eluting ligand. Removal of the ligand and reactivation of the enzyme is classically accomplished by dialysis or diafiltration, but special considerations apply to the present class of inhibitors. Two synergistic chemical approaches were taken instead. These involve conversion of the inhibitor to its oxime, and blockade of the enzyme active site thiol by thiol-disulfide interchange with oxidized glutathione.

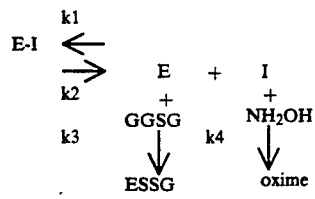

The rate of reactivation of enzyme is governed by the rate of dissociation of E-I complex to form free enzyme and inhibitor ($K_2 = 1 \times 10^{-4}$ sec$^{-1}$), the rate of oxime formation ($K_4 = 7.7 \pm 1.7 \times 10^{-2}$M$^{-1}$ sec$^{-1}$), and the rate of thiol-disulfide interchange between the free enzyme and glutathione disulfide ($K_3 = 3$M$^{-1}$ sec$^{-1}$).

Product can be obtained by use of either of these techniques alone, however they are preferably used in tandem. The application of glutathione in this context gives a mixed disulfide that can be reversibly reactivated by reduction with dithiothreitol or other free thiol. There is no known precedent for this selective protection by glutathione of an enzyme. On the other hand, the conversion of aldehydes to their oximes by reaction with hydroxylamine dates from the nineteenth century. Rate constants for oxime formation ($K_4$), and thiol-disulfide interchange with glutathione disulfide ($K_3$) were measured by us. These rate constants were used to predict optimal concentrations of glutathione disulfide and hydroxylamine: those above which dissociation of enzyme-inhibitor complex becomes rate limiting. The simultaneous application of both approaches is necessary to achieve the highest level of reactivation. The oxidation and/or conversion can be accomplished by any of the standard methods available for such reactions. See H. R. Mahler and E. H. Cordes, *Biological Chemistry*, Harper and Row, New York (1971). W. P. Jencks, Catalysis in Chemistry and Enzymology, McGraw-Hill, New York (1969). Based on the above rate constants, we have found addition of 100 mM hydroxylamine and 10 mM glutathione disulfide to be adequate. The reaction may be allowed to go until essentially complete in about 16 hours (10 halflives).

After reactivation is complete, the low molecular weight products and excess reactants can be removed by traditional dialysis or ultrafiltration. Using an Amicon Centricon-10 ultrafiltration cell, we typically carry out 5 exchanges with the chromatography buffer, which reduces their concentrations to nanomolar levels. This gives the glutathione conjugate of the purified enzyme. When desired, the conjugate can be reduced with 10 mM dithiothreitol (halflife 1 min) or any other free thiol to give active enzyme. In either state, the purified enzyme is stable indefinitely at −80° C.

Compounds of the instant invention are conveniently prepared using the procedures described generally below and more explicitly described in the Example section thereafter.

SCHEME 1

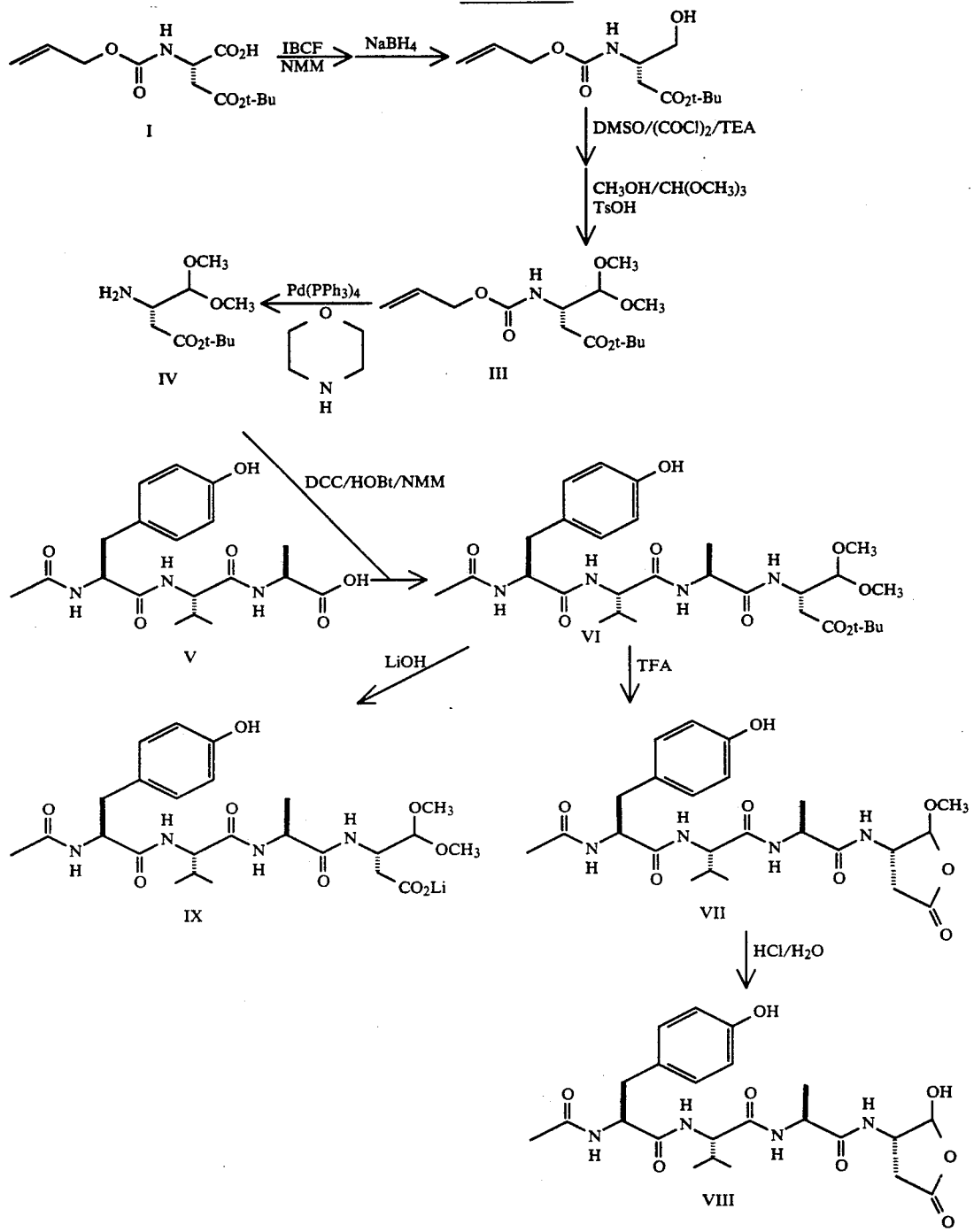

The reactions of Scheme I proceed as follows. A mixed anhydride of allyloxycarbonyl (Alloc)-(S)-aspartic acid β-t-butyl ester with isobutylchloroformate (IBCF) is formed in the presence of N-methylmorpholine (NMM). This anhydride is reduced to the corresponding alcohol II using sodium borohydride at 0° C. in a solvent of 4:1 tetrahydrofuran (THF):methanol. The alcohol II is then oxidized using dimethyl sulfoxide (DMSO), oxallyl chloride, and triethyl amine to the corresponding aldehyde which is protected as the dimethyl acetal using methanol, trimethyl orthoformate and p-toluenesulfonic acid to afford III. The Alloc protecting group is then removed with tetrakis triphenylphosphine palladium in the presence of morpholine to afford amine IV. This amine is then coupled to the tripeptide, N-acetyl-(S)-tyrosinyl-(S)-alanine valinyl-(S)- using dicyclohexyl carbodiimide (DCC) in the presence of hydroxybenzotriazole (HOBt), and NMM to afford VI. The t-butyl ester is then removed with neat TFA to provide the cyclic O-methylacylal VII. The final hydrolysis is accomplished with dilute hydrochloric acid in 1:1 water:methanol to give VIII. In addition, VI can be saponified with LiOH to give the dimethyl acetal IX.

SCHEME II

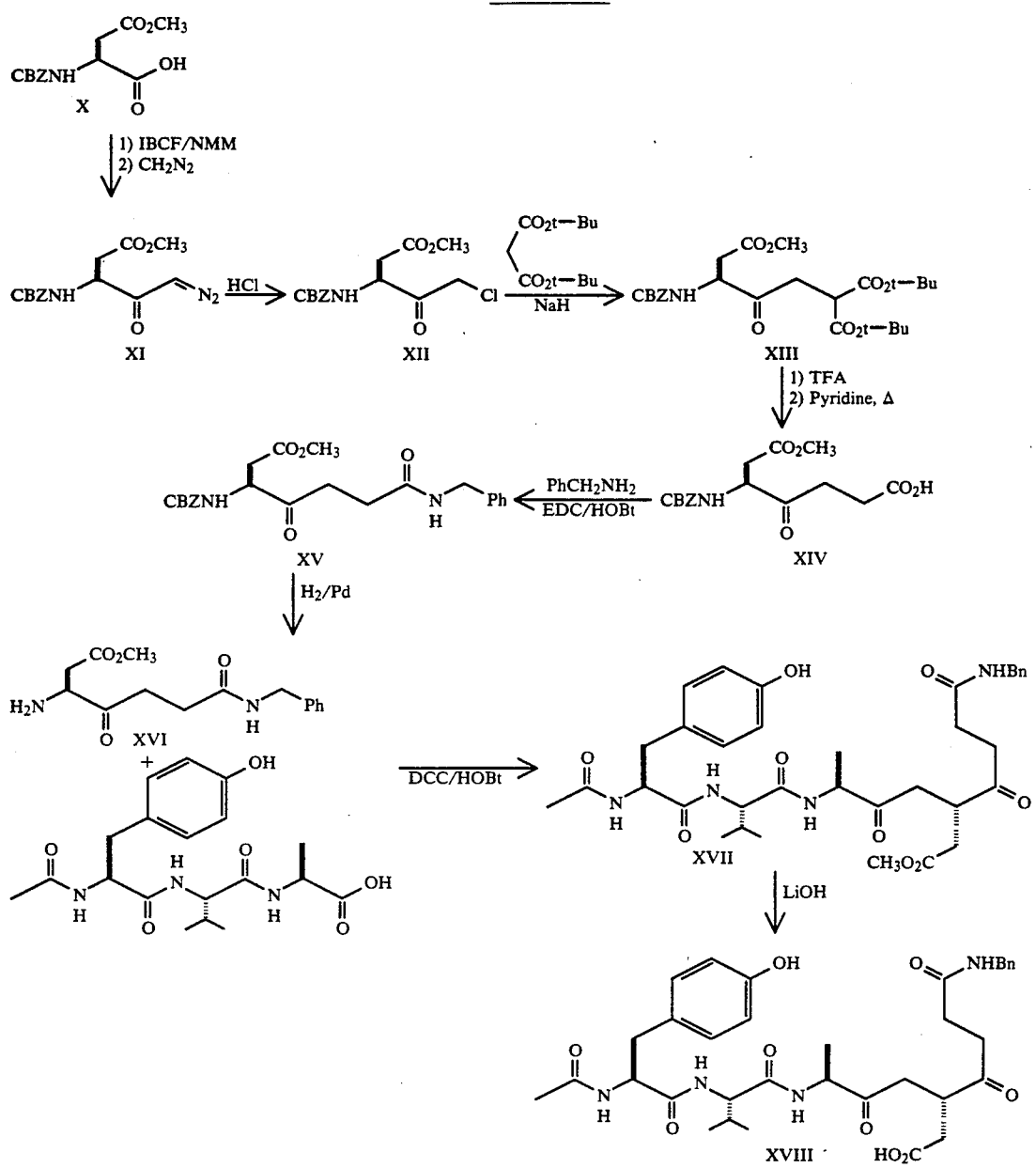

Structures such as XVIII can be prepared as shown in scheme II. N-CBZ-Aspartic acid β-methyl ester can be treated with i-butylchloroformate in the presence of N-methylmorpholine (NMM) followed by diazomethane to afford diazomethylketone XI. Treatment of XI with hydrochloric acid gives chloromethylketone XII, which can be used to alkylate the sodium salt of di-t-butyl malonate to give ketodiester XIII. The t-butyl groups can be removed with trifluoroacetic acid and the resultant dicarboxylic acid can be decarboxylated in hot pyridine to afford keto acid XIV. Acid XIV can then be coupled to benzyl amine using ethyldimethylaminopropyl carbodiimide in the presence of hydroxybenzotriazole (HOBt) to afford amide XV. Removal of the CBZ group is accomplished with hydrogen in the presence of 10% palladium on carbon to give amine XVI. This amine can then be coupled to N-acetyltyrosinyl-valinyl-alanine using dicyclohexyl carbodiimide in the presence of HOBt to afford XVII. Final deprotection of the carboxylic acid can be accomplished with lithium hydroxide to afford the desired ICE inhibitor XVIII.

The compounds of the instant invention of the formula (I), as represented in the Examples hereinunder shown to exhibit in vitro inhibitory activities with respect to interleukin-1β. In particular, these compounds have been shown to inhibit interleukin-1β converting enzyme from cleaving precursor interleukin-1β as to form active interleukin-1β at a Ki of less than 1 uM.

SCHEME III

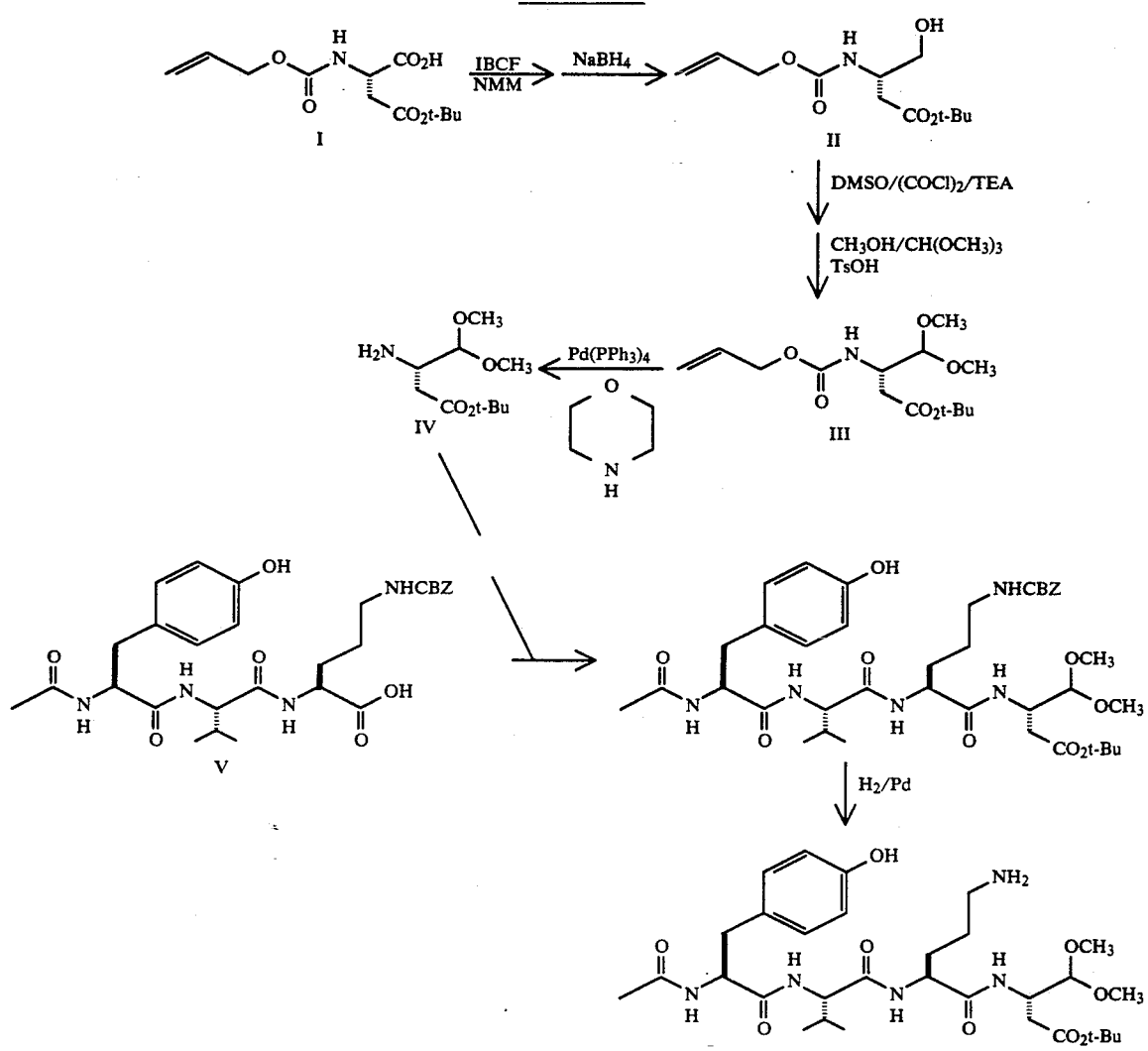

The reactions of Scheme III proceed as follows. A mixed anhydride of allyloxy-carbonyl(Alloc) (S)-aspartic acid b-t-butyl ester with isobutylchloroformate (IBCF) is formed in the presence of N-methylmorpholine (NMM). This anhydride is reduced to the corresponding alcohol using sodium borohydride at 0° C. in a solvent of 4:1 tetrahydrofuran (THF):methanol. The alcohol is then oxidized using dimethyl sulfoxide (DMSO), oxallyl chloride, and triethyl amine to the corresponding aldehyde which is protected as the dimethyl acetal using methanol, trimethyl orthoformate and p-tolunesulfonic acid. The Alloc protecting group is then removed with tetrakis triphenylphosphine palladium in the presence of morpholine and the resulting amine is then coupled to the tripeptide, N-acetyl-(S)-tyrosinyl-(S)valinyl-(S)-CBZ)-lysine using dicyclohexyl carbodiimide (DCC) in the presence of hydroxybenzotriazole (HOBt), and NMM. The CBZ group is then removed with Pearlman's catalyst (Pd(OH)$_2$ on carbon) in the presence of hydrogen to afford the desired protected affinity ligand.

SCHEME IV

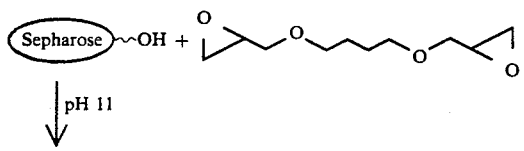

SCHEME IV -continued

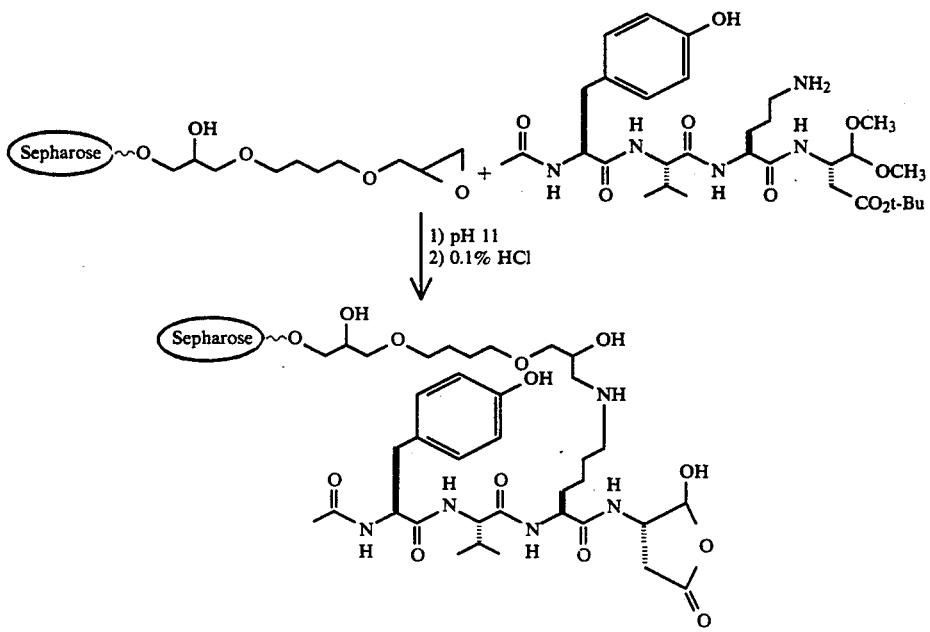

An affinity column for the purification of IL-1β converting enzyme can be prepared as shown in scheme IV. Sepharose is coupled to 1,4-butanediol diglycidyl ether at pH 11. The resulting resin bound epoxide reacts with the precursor affinity ligand at pH 11 and 37° C. During this process, the t-butyl ester is saponified. The deprotection of the dimethyl acetal is accomplished with dilute hydrochloric acid to afford the desired affinity matrix.

The following Examples are intended to illustrate the invention and as such are not intended to limit the invention as set forth in the claims appended, thereto.

EXAMPLE 1

Preparation of a chromatographic matrix from Compound A

An affinity column for interleukin-1 converting enzyme was prepared from the potent peptide aldehyde inhibitor Acetyl-Tyr-Val-Lys-Asp-CHO (Compound A), coupled via a 12-atom bis-oxirane spacer to SEPHAROSE CL-4B through the lysine residue.

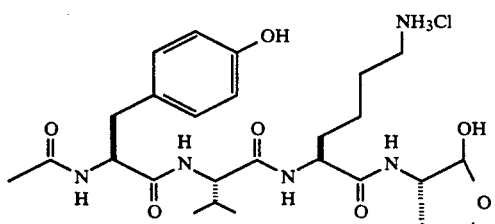

Synthesis of Affinity Matrix

Step A: Epoxy-activated SEPHAROSE CL-4B:

Epoxy-activated SEPHAROSE CL-4B was prepared as described in the literature (Sundberg, L., and Porath, J. (1974) J. Chromatogr. 90, 87-98). Specifically, a slurry consisting of 100 gm suction-dried SEPHAROSE CL-4B, 100 ml of 1,4-butanediol diglycidyl ether (a nominal 70% solution), and 100 ml 0.6M NaOH containing 2 mg/ml NaBH4 was mixed with an overhead stirrer for 16 hours at ambient temperature. The resulting epoxy-activated SEPHAROSE CL-4B was washed exhaustively on a coarse sintered glass funnel with 10 liters of water, and stored in water at 4° C.

Step B: Coupling of Peptide Aldehyde Dimethyl Acetal:

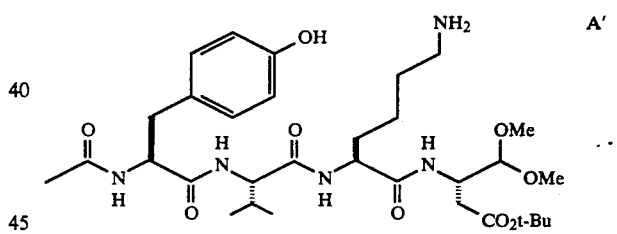

The blocked aspartyl-t-butyl ester, dimethyl acetal (Compound A') of the active aldehyde, Compound A, was dissolved as a 10 mM solution in methanol, and then combined with more methanol, water, and a 400 mM sodium carbonate solution adjusted to pH 11.00 with HCL, to give a 50% methanol solution containing 2 mM inhibitor and 200 mM carbonate buffer. This solution (10 ml) was mixed with the suction-dried cake (10 gm) of epoxy-activated SEPHAROSE CL-4B, and the slurry was stirred by rotation at 37° C. for 3 days. The resulting affinity matrix was washed thoroughly with 1M KCl and water, and was stored as a slurry at 4° C. The incorporation, based on results with [14-C]-lisinopril (Bull, H. G., Thornberry, N. A., and Cordes, E. H. (1985) J. Biol. Chem. 260, 2963-2972), is estimated to be 1 umol/ml packed affinity matrix.

Step C: Activation to Aldehyde:

The above procedure gave the dimethyl-acetal of Acetyl-Tyr-Val-Lys-Asp-CHO coupled to the spacer arm, the t-butyl protecting group on the aspartate residue being lost during the coupling conditions. Activation of this matrix to the aldehyde was carried out in the affinity column just prior to use, by equilibrating the matrix with 0.01N HCl and letting it stand for 2 hours at 25° C. A control matrix containing [14-C]glycine as a tracer gave no evidence (<1%) for loss of ligand under these conditions.

EXAMPLE 2

Affinity Chromatography Procedure

The starting enzyme preparation was purified ~100-fold from THP-1 cell lysate by anion exchange chromatography as described in Example 4.

Step A: Binding of ICE:

The activated affinity column (5 ml, 1 cm×6.5 cm) and a guard column of native SEPHAROSE CL-4B of equal dimensions were equilibrated with 10 column volumes of the chromatography buffer (100 mM hepes, 10% sucrose, and 0.1% 3-[(3-cholamidopropyl)dimethylammonio]-1-propanesulfonate (CHAPS) at pH 7.50) supplemented with 1 mM dithiothreitol. The enzyme solution (15 ml, 150,000 units, 150 mg protein) was applied through the guard column and run onto the affinity column at a flow rate of 0.022 ml/min at 4° C., and washed through with an additional 10 ml chromatography buffer at the same flow rate. During loading, 8% of the enzymatic activity was not retained, presumably due to the slow rate constant for binding. After loading, the guard column was removed and the affinity column was washed with 25 column volumes of buffer at a faster flow rate of 0.5 ml/min at 4° C. No enzymatic activity was detected in the wash fractions.

Step B: Elution of Bound ICE:

To elute the enzyme, the column was then flooded with 1 column volume of buffer containing 200 μM Acetyl-Tyr-Val-Lys(CBZ)-Asp-CHO (Compound B), and left for 24 hours at room temperature to achieve dissociation of the matrix-bound enzyme. The free enzyme-inhibitor complex was then recovered from the affinity column by washing with 2 column volumes of buffer at a flow rate of 0.022 ml/min. Repeating the exchange with fresh inhibitor produced <5% more enzyme, indicating that the first exchange had been adequate.

Step C: Reactivation of ICE:

The eluted ICE was reactivated using two synergistic chemical approaches: conversion of the inhibitor to its oxime, and oxidation of the active site thiol to its mixed disulfide with glutathione by thiol-disulfide interchange.

The enzyme-inhibitor solution recovered from the affinity column was adjusted to contain 100 mM neutral hydroxylamine and 10 mM glutathione disulfide to effect reactivation. Under these conditions, after a short lag with a halflife of 100 sec for consumption of excess free inhibitor, the dissociation of E-I complex is entirely rate determining with a halflife of ~100 min at 25° C. After allowing 10 halflives for the exchange, the inhibitor oxime and excess reagents were removed by exhaustive desalting in an AMICON CENTRICON-10 ultrafiltration cell using the chromatography buffer at 4° C. When desired, the enzyme-glutathione conjugate was reduced with 10 mM dithiothreitol (halflife <1 min) to give active enzyme. The purified enzyme is stable indefinitely at −80° C. The recovery of enzymatic activity by affinity chromatography was >90%, and the purification achieved was ~5,000-fold, as measured by SDS-polyacrylamide gel electrophoresis. The results are summarized in Table 1.

TABLE 1

| AFFINITY PURIFICATION OF ICE | | | | | |
|---|---|---|---|---|---|
| | vol. ml | units | units ml | mg | mg/ml | units mg |
| DEAE sample | 15 | 150,000 | 10 | 150 | 10 | 1000 |
| Affinity Eluate | 0.2 | 140,000 | 700 | 0.03* | 0.15 | 4.7 × 10⁶ |
| | | recovery = 93% | | | | |
| | | ·purification = 4700-fold | | | | |

*Estimated from silver staining intensity on SDS-PAGE

EXAMPLE 3

Purification from Crude Lysate

The affinity matrix of Example 1 has also been used to purify enzyme directly to homogeneity from crude cell lysate. In this alternative, 7.5 ml of concentrated THP-1 cell lysate (prepared as described in Example 4) was applied to a 500 ul affinity column protected by a 5 ml SEPHAROSE CL-4B guard column. After rinsing the affinity column with 10 column volumes of buffer, the enzyme was eluted as described in Example 2. ~100-fold purification has been achieved at this point, as measured by SDS-polyacrylamide gel electrophoresis washing, reflecting insufficient rinsing. The recovered enzyme was reactivated as above, and rechromatographed on a fresh affinity column using a more extensive rinse. Elution now gave homogeneous enzyme, equivalent to >100,000-fold overall purification.

EXAMPLE 4

Step A: Cell Growth:

THP.1 cells obtained from the ATCC (accession number ATCC TIB202) were grown in suspension in ISCOVE'S MODIFIED DULBECCO'S MEDIUM or in DULBECCO'S MODIFIED EAGLE'S MEDIUM (JRH BIOSCIENCES) with 9% horse serum in either roller bottles, WHEATON TURBOLIFT 46 liter suspension flasks, or in 75, 200, or 300 liter fermenters with weekly harvests at 1–2×10⁶ cells/ml (3–4 doublings/week). Media used in suspension flasks or fermenters also contained 0.1–0.3% F68 pluronic to reduce shear force on the cells. Cells were typically grown for no more than 3–4 months following initial startup from the ATCC vial.

Step B: Cell Breakage and Fractionation:

Cells were washed 3 times in PBS and suspended 20 minutes at 0° C. at 10⁸ cells/ml in a hypotonic buffer containing 25 mM HEPES, pH 7.5, 5 mM MgCl₂, and 1 mM EGTA. Protease inhibitors were added (1 mM PMSF and 10 μg/ml of pepstatin and leupeptin), and the cells were broken in 100 or 300 ml tight fitting DOUNCE homogenizers using 25 or 15 strokes respectively to yield 90–95% breakage. The broken cells were centrifuged at 3000 rpm, 10 minutes, 5° C. in a BECKMAN GPR centrifuge to remove nuclei and unbroken cells. The resultant pellet was resuspended in about ¼ the original volume of the hypotonic buffer with the protease inhibitors, and the suspension was reDounced for 10 strokes and recentrifuged. This second postnuclear supernatant was added to the first.

The postnuclear supernatant was centrifuged for 20 minutes, 16,000 rom in a SORVAL centrifuge with an SS34 rotor followed by a second spin for 60 minutes at 50,000 rpm in a BECKMAN centrifuge (50.2 Ti rotor) or 45,000 rpm (45 Ti rotor). After addition of 2 mM DTT, the resultant supernatant was stored at −80° C. until purification of ICE.

Step C: HPLC Column Purification of ICE:

The thawed supernatants were clarified by 0.22μ hollow fiber filtration and concentrated 10-20 fold with an AMICON YM3 spiral cartridge and dialyzed overnight (8000 molecular weight cutoff dialysis membrane) vs a buffer of 20 mM TRIS, pH 7.8, 10% sucrose, 0.1% CHAPS, and 2 mM DTT. The dialyzed supernatant (ca. 3-5 g total protein, corresponding to 1000 ml of cytosolic extract) was adjusted to less than 500 MICRP-SIEMANS conductivity with water and applied to a 475 ml bed volume DEAE-5PW HPLC (BIORAD) column. ICE was eluted at about 40 mM NaCl in a gradient with the same buffer and increasing proportions of 0.5M NaCl and 220 mM Tris HCl. The ICE active fractions were assayed using a 96 well plate fluorometric assay with a 100 μl volume containing 100 μM YVAD-AMC substrate in a buffer of 25 mM HEPES, pH 7.5, 10% sucrose, 0.1% CHAPS, and 2 mM DTT.

The ICE active fractions from the DEAE column were pooled, diluted with an equal volume of the HEPES, sucrose, CHAPS, DTT buffer, adjusted to pH 7.0, and applied to a 150 ml bed volume SP-5PW HPLC (BIORAD) column and eluted at about 85 nM in a KCl gradient with the same buffer. The ICE active fractions were chromatographed by SDS-PAGE (10-20, 17-27, 16, or 18% gels) and silver stained to determine the bands that tracked with activity. These SP-HPLC fractions were also further chromatographed on a C4-narrowbore (ABI) HPLC column eluted with an acetonitrile gradient in 0.0% TFA.

EXAMPLE 5

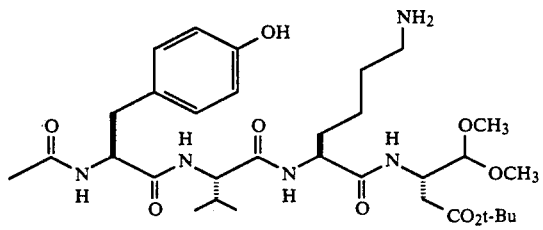

N-(N-Acetyl-tyrosinyl-valinyl-lysinyl)-3-amino-4-oxobutanoic acid dimethyl acetal b-t-butyl ester.

Step A:
N-allyloxycarbonyl-3-amino-4-hyroxybutanoic acid tert-butyl ester.

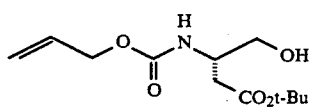

To a solution of N-allyloxycarbonyl (S)-aspartic acid b-tert-butyl ester (2.00 g, 7.32 mmol) in 50 mL of tetrahydrofuran (THF) at 0° C., was added N-methyl morpholine (NMM, 885 mL, 8.05 mmol) followed by isobutyl chloroformate (IBCF, 997 mL, 7.68 mmol). After 15 min, this mixture was added to a suspension of sodium borohydride (550 mg, 14.55 mmol) in 50 mL of THF anf 12.5 mL of methanol at −45° C. After 30 min at −45° C., the mixture was warmed to 0° C. and held at that temperature for 30 min. The reaction was quenched with acetic acid, diluted with 1:1 ethyl acetate:hexane, and washed 3 times with dilute sodium bicarbonate. The organics were dried over sodium sulfate, filtered, and concentrated. The residue was purified by MPLC on silica-gel (35×350 mm column, 30% ethyl acetate/hexane) to give the desired product: $^1$H NMR (200 MHz, CD$_3$OD) d 5.9 (m, 1H), 5.28 (br d, 1H, J=17 Hz), 5.15 (br d, 1H, J=9 Hz), 4.52 (br d, 2H, J=6 Hz), 3.98 (m, 1H), 3.48 (ABX, 2H, J=5, 6, 11 Hz), 2.53 (dd, 1H, J=5, 16 Hz), 2.32 (dd, 1H, J=9, 16 Hz), 1.43 (s, 9H).

Step B:
N-allyloxycarbonyl-3-amino-4-oxobutanoic acid b-tert-butyl ester dimethyl acetal.

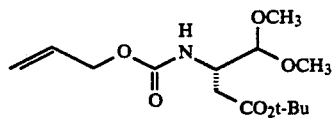

To a solution of dimethyl sulfoxide (757 mL, 10.67 mmol) in 10 mL of dichloromethane at −45° C. was added oxalyl chloride (508 mL, 5.82 mmol). After 5 min, a solution of N-allyloxycarbonyl-3-amino-4-hyroxybutanoic acid tert-butyl ester (1.25 g, 4.85 mmol) in 10 mL of dichloromethane was added. After 15 min, triethyl amine (2.03 mL, 14.55 mmol) was added. After 30 min, the mixture was warmed to −23° C. and stirred for 30 min. The mixture was diluted with 1:1 ethyl acetate/hexane, washed with water, 1N sodium hydrogensulfate, and twice with water. The organics were dried over sodium sulfate, filtered, and concentrated. The resultant oil was dissolved in 200 mL of methanol and 20 mL of trimethyl orthoformate and 100 mg of p-toluene sulphonic acid were added. After 16 hours, the reaction was quenched with saturated sodium bicarbonate and concentrated in vacuo. The mixture was diluted with ether and washed 5 times with dilute sodium bicarbonate. The ether layer was dried over magnesium sulfate, filtered, and concentrated to afford the title compound as a colorless oil: $^1$H NMR (200 MHz, CD$_3$OD) d 5.9 (m, 1H), 5.26 (br d, 1H, J=17 Hz), 5.14 (br d, 1H, J=10 Hz), 4.51 (br d, 2H, J=5.33 Hz), 4.25 (d, 1H, J=4.79 Hz), 4.11 (m, 1H), 3.40 (s, 3H), 3.39 (s, 3H), 2.52 (dd, 1H, J=4.86, 15.27 Hz), 2.30 (dd, 1H, J=9.00, 15.28 Hz), 1.43 (s, 9H).

Step C:
3-Amino-4-oxobutanoic acid b-tert-butyl ester dimethyl acetal.

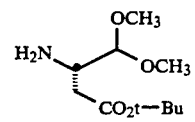

To a solution of N-allyloxycarbonyl-3-amino-4-oxobutanoic acid b-tert-butyl ester dimethyl acetal (312 mg, 1.03 mmol) in 10 mL of THF was added morpholine (897 mL, 10.3 mmol) and tetrakis triphenylphosphine palladium (100 mg). After 3 hours, the mixture was diluted with 1:1 ethyl acetate/hexane and washed 5 times with dilute sodium bicarbonate. The organs were dried over sodium sulfate, filtered, and concentrated. The resulting oil was purified by MPLC on silica-gel (22×300 mm column, linear gradient of dichloromethane to 1% ammonia and 10% methanol in dichloromethane) to afford the title compound as a pale-yellow oil: $^1$H NMR (200 MHz, CD$_3$OD) d 4.15 (d, 1H, J=5.67 Hz), 3.41 (s, 3H), 3.40 (s, 3H), 3.19 (m, 1H), 2.47 (dd, 1H, J=4.88, 16.06 Hz), 2.22 (dd, 1H, J=7.86, 16.16 Hz), 1.45 (s, 9H).

Step D:

N-(N-Acetyl-tyrosinyl-valinyl-(e-CBZ-lysinyl))-3-amino-4-oxobutanoic acid b-tert-butyl ester dimethyl acetal.

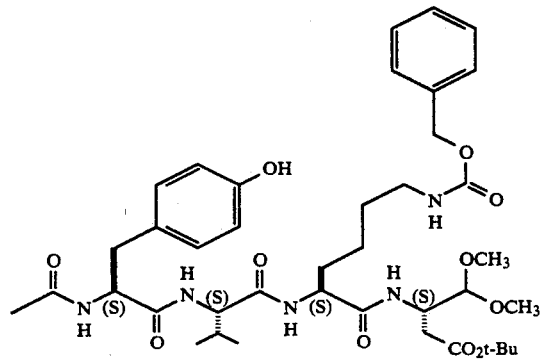

To a solution of 3-Amino-4-oxobutanoic acid b-tert-butyl ester dimethyl acetal (238 mg, 1.09 mmol) in 5 mL of DMF at 0° C. was added N-methyl morpholine (599 mL, 5.45 mmol) followed sequentially by N-Acetyl-tyrosinyl-valinyl-e-CBZ-lysine (735 mg, 1.09 mmol), hydroxybenzotriazole (221 mg, 1.64 mmol), and dicyclohexylcarbodiimide (225 mg, 1.09 mmol). After 16 hours at ambient temperature, the mixture was filtered and purified by Sephadex" LH-20 chromatography (1M×50 mm column, methanol eluent). The resulting product was further purified by MPLC on silica-gel (22×300 mm column, eluting with a linear gradient of dichloromethane to 1% ammonia and 10% methanol in dichloromethane) to give the title compound as a colorless solid: $^1$H NMR (200 MHz, CD$_3$OD) d 7.31 (br s, 5H), 7.04 (br d, 2H, J=8.35 Hz), 6.67 (br d, 2H, J=8.45 Hz), 5.04 (s, 2H), 4.61 (m, 1H), 4.44–4.25 (m, 3H), 4.17 (d, 1H, J=7.27 Hz), 3.39 (s, 3H), 3.38 (s, 3H), 3.1–2.9 (m, 3H), 2.75 (dd, 1H, J=9.28, 14.12 Hz), 2.53 (dd, 1H, J=5.47, 15.58 Hz), 2.33 (dd, 1H, J=7.96, 15.53 Hz), 2.04 (m, 1H), 1.88 (s, 3H), 1.8–1.2 (m, 6H), 1.41 (s, 9H), 0.94 (d, 6H, J=6.74 Hz).

Step E:

N-(N-Acetyl-tyrosinyl-valinyl-lysinyl)-3-amino-4-oxobutanoic acid dimethyl acetal b-t-butyl ester.

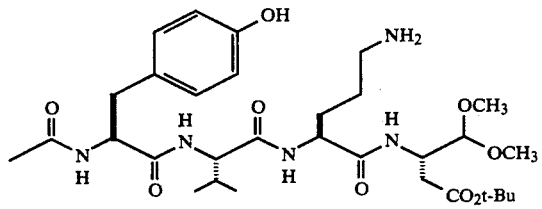

A solution of N-(N-Acetyl-tyrosinyl-valinyl-e-CBZ-lysinyl)-3-amino-4-oxobutanoic acid b-tert-butyl ester dimethyl acetal (15.6 mg) was dissolved in 2 mL of methanol and 10 mg of Pearlman's catalyst (Pd(OH)$_2$ on Carbon) was added. After 30 min under hydrogen, the mixture was filtered and concentrated to give the title compound: $^1$H NMR (200 MHz, CD$_3$OD) d 7.04 (br d, 2H, J=8.44 Hz), 6.67 (br d, 2H, J=8.54 Hz), 4.57 (dd, 1H, J=5.23, 9.04 Hz), 4.5–4.0 (m, 4H), 3.38 (s, 3H), 3.34 (s, 3H), 3.02 (dd, 1H, J=5.17, 13.81 Hz), 2.75 (dd, 1H, J=9.23, 14.06 Hz), 2.66 (t, 2H, J=7.08 Hz), 2.53 (dd, 1H, J=5.47, 15.58 Hz), 2.34 (dd, 1H, J=7.91, 15.57 Hz), 2.03 (m, 1H), 1.88 (s, 3H), 1.9–1.2 (m, 6H), 1.41 (s, 9H), 0.94 (d, 6H, J=6.69 Hz), 0.93 (d, 3H, J=6.64 Hz).

EXAMPLE 6

N-(N-Acetyl-tyrosinyl-valinyl-alaninyl)-3-amino-4-oxobutanoic acid.

Step A:

N-allyloxycarbonyl-3-amino-4-hyroxybutanoic acid tert-butyl ester.

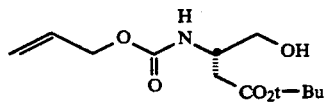

To a solution of N-allyloxy-carbonyl (S)-aspartic acid β-tert-butyl ester (2.00 g, 7.32 mmol) in 50 mL of tetrahydrofuran (THF) at 0° C., was added N-methyl morpholine (NMM, 885 mL, 8.05 mmol) followed by isobutyl chloroformate (IBCF, 997 mL, 7.68 mmol). After 15 minutes, this mixture was added to a suspension of sodium borohydride (550 mg, 14.55 mmol) in 50 mL of THF anf 12.5 mL of methanol at −45° C. After 30 minutes at −45° C., the mixture was warmed to 0° C. and held at that temperature for 30 minutes. The reaction was quenched with acetic acid, diluted with 1:1 ethyl acetate:hexane, and washed 3 times with dilute sodium bicarbonate. The organics were dried over sodium sulfate, filtered, and concentrated. The residue was purified by MPLC on silica-gel (35×350 mm column, 30% ethyl acetate/hexane) to give the desired product: $^1$H NMR (200 MHz, CD$_3$OD) δ5.9 (m, 1H), 5.28 (br d, 1H, J=17 Hz), 5.15 (br d, 1H, J=9 Hz), 4.52 (br d, 2H, J=6 Hz), 3.98 (m, 1H), 3.48 (ABX, 2H, J=5, 6, 11 Hz), 2.53 (dd, 1H, J=5, 16 Hz), 2.32 (dd, 1H, J=9, 16 Hz), 1.43 (s, 9H).

Step B:

N-allyloxycarbonyl-3-amino-4-oxobutanoic acid β-tert-butyl ester dimethyl acetal.

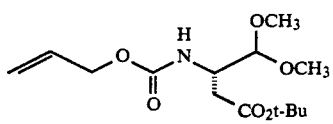

To a solution of dimethyl sulfoxide (757 mL, 10.67 mmol) in 10 mL of dichloromethane at −45° C. was added oxalyl chloride (508 mL, 5.82 mmol). After 5 minutes, a solution of N-allyloxycarbonyl-3-amino-4-hyroxybutanoic acid tert-butyl ester (1.25 g, 4.85 mmol) in 10 mL of dichloromethane was added. After 15 minutes, triethyl amine (2.03 mL, 14.55 mmol) was added. After 30 minutes, the mixture was warmed to −23° C. and stirred for 30 minutes. The mixture was diluted with 1:1 ethyl acetate/hexane, washed with water, 1N sodium hydrogensulfate, and twice with water. The organics were dried over sodium sulfate, filtered, and concentrated. The resultant oil was dissolved in 200 mL of methanol and 20 mL of trimethyl orthoformate and 100 mg of p-toluene sulphonic acid were added. After 16 hours, the reaction was quenched with saturated sodium bicarbonate and concentrated in vacuo. The mixture was diluted with ether and washed 5 times with dilute sodium bicarbonate. The ether layer was dried over magnesium sulfate, filtered, and concentrated to afford the title compound as a colorless oil: $^1$H NMR (200 MHz, CD$_3$OD) δ5.9 (m, 1H), 5.26 (br d, 1H, J=17 Hz), 5.14 (br d, 1H, J=10 Hz), 4.51 (br d, 2H, J=5.33 Hz), 4.25 (d, 1H, J=4.79 Hz), 4.11 (m, 1H), 3.40 (s, 3H), 3.39 (s, 3H), 2.52 (dd, 1H, J=4.86, 15.27 Hz), 2.30 (dd, 1H, J=9.00, 15.28 Hz), 1.43 (s, 9H).

Step C:

3-Amino-4-oxobutanoic acid β-tert-butyl ester dimethyl acetal.

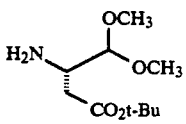

To a solution of N-allyloxy-carbonyl-3-amino-4-oxobutanoic acid β-tert-butyl ester dimethyl acetal (312 mg, 1.03 mmol) in 10 mL of THF was added morpholine (897 mL, 10.3 mmol) and tetrakis triphenylphosphine palladium (100 mg). After 3 hours, the mixture was diluted with 1:1 ethyl acetate/hexane and washed 5 times with dilute sodium bicarbonate. The organics were dried over sodium sulfate, filtered, and concentrated. The resulting oil was purified by MPLC on silica-gel (22×300 mm column, linear gradient of dichloromethane to 1% ammonia and 10% methanol in dichloromethane) to afford the title compound as a pale-yellow oil: $^1$H NMR (200 MHz, CD$_3$OD) δ4.15 (d, 1H, J=5.67 Hz), 3.41 (s, 3H), 3.40 (s, 3H), 3.19 (m, 1H), 2.47 (dd, 1H, J=4.88, 16.06 Hz), 2.22 (dd, 1H, J=7.86, 16.16 Hz), 1.45 (s, 9H).

Step D

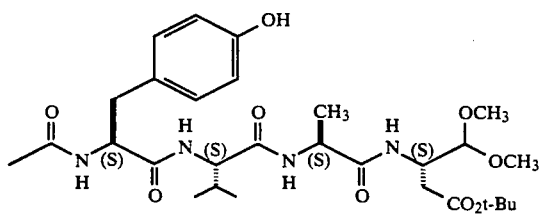

N-(N-Acetyl-tyrosinyl-valinyl-alaninyl)-3-amino-4-oxobutanoic acid β-tert-butyl ester dimethyl acetal.

To a solution of 3-Amino-4-oxobutanoic acid β-tert-butyl ester dimethyl acetal (104 mg, 0.473 mmol) in 3 mL of DMF at 0° C. was added N-methyl morpholine (260 mL, 2.37 mmol) followed sequentially by N-Acetyl-tyrosinyl-valinyl-alanine (229 mg, 0.473 mmol), hydroxybenzotriazole (96 mg, 0.710 mmol), and dicyclohexylcarbodiimide (98 mg, 0.473 mmol). After 24 hours at ambient temperature, the mixture was filtered and purified by SEPHADEX LH-20 chromatography (1M×50 mm column, methanol eluent). The resulting product was further purified by MPLC on silica-gel (22×300 mm column, eluting with a linear gradient of dichloromethane to 1% ammonia and 10% methanol in dichloro methane) to give the title compound as a colorless solid: $^1$H NMR (200 MHz, CD$_3$OD) δ7.04 (br d, 2H, J=8.54 Hz), 6.67 (br d, 2H, J=8.57 Hz), 4.58 (dd, 1H, J=5.61, 9.03), 4.4–4.2 (m, 3H), 4.16 (d, 1H, J=7.12 Hz), 3.39 (s, 3H), 3.38 (s, 3H), 3.01 (dd, 1H, J=5.54, 13.97 Hz), 2.76 (dd, 1H, J=8.89, 13.90 Hz), 2.53 (dd, 1H, J=5.50, 14.45 Hz), 2.34 (dd, 1H, J=7.83, 15.49 Hz), 2.05 (m, 1H), 1.90 (s, 3H), 1.41 (s, 9H), 1.33 (d, 3H, J=7.16 Hz), 0.94 (d, 3H, J=6.73 Hz), 0.92 (d, 3H, J=6.77 Hz).

Step E

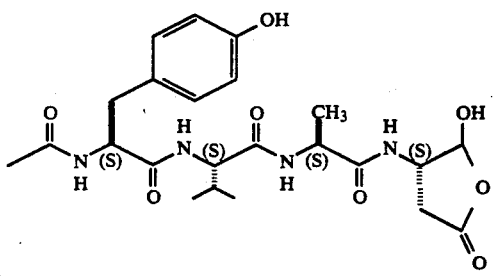

N-(N-Acetyl-tyrosinyl-valinyl-alaninyl)-3-amino-4-oxobutanoic acid. A solution of N-(N-Acetyl-tyrosinyl-valinyl-alaninyl)-3-amino-4-oxobutanoic acid β-tert-butyl ester dimethyl acetal (17.4 mg) in 2 mL of trifluoroacetic acid was aged for 15 minutes and concentrated in vacuo. The product was dissolved in 1.0 mL of methanol and 1.0 mL of water containing 60 uL of thionyl chloride was added. After 2 hours, the pH of the solution was adjusted to around 5 with sodium acetate to afford a solution of the title compound: $^1$H NMR (200 MHz, CD$_3$OD) δ7.08 (br d, 2H, J=8.44 Hz), 6.76 (br d, 2H, J=8.49 Hz), 4.7–4.1 (m, 4H), 4.04 (d, 1H, J=7.67 Hz), 3.05–2.40 (m, 4H), 2.05 (m, 1H), 1.96 (s, 3H), 1.35 (d, 3H, J=7.23 Hz), 0.89 (d, 6H, J=6.84 Hz).

EXAMPLE 7

N-(N-Acetyl-tyrosinyl-valinyl-ε-CBZ-lysinyl)-3-amino-4-oxobutanoic acid.

Step A

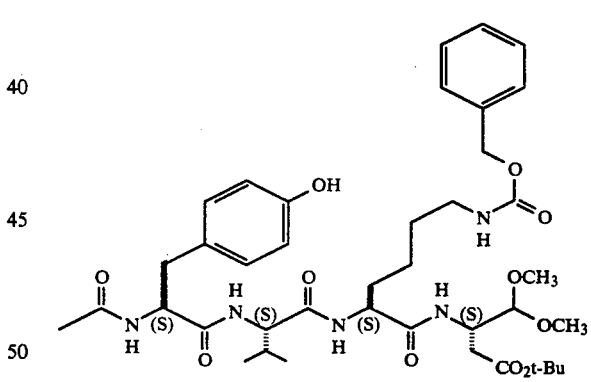

N-(N-Acetyl-tyrosinyl-valinyl-(ε-CBZ-lysinyl))-3-amino-4-oxobutanoic acid β-tert-butyl ester dimethyl acetal. To a solution of 3-Amino-4-oxobutanoic acid β-tert-butyl ester dimethyl acetal (238 mg, 1.09 mmol) in 5 mL of DMF at 0° C. was added N-methyl morpholine (599 mL, 5.45 mmol) followed sequentially by N-Acetyl-tyrosinyl-valinyl-ε-CBZ-lysine (735 mg, 1.09 mmol), hydroxybenzotriazole (221 mg, 1.64 mmol), and dicyclohexylcarbodiimide (225 mg, 1.09 mmol). After 16 hours at ambient temperature, the mixture was filtered and purified by SEPHADEX LH-20 chromatography (1M×50 mm column, methanol eluent). The resulting product was further purified by MPLC on silica-gel (22×300 mm column, eluting with a linear gradient of dichloromethane to 1% ammonia and 10% methanol in dichloromethane) to give the title compound as a colorless solid: $^1$H NMR (200 MHz, CD$_3$OD) δ7.31 (br s, 5H), 7.04 (br d, 2H, J=8.35 Hz), 6.67 (br d, 2H, J=8.45 Hz), 5.04 (s, 2H), 4.61 (m, 1H), 4.44–4.25 (m, 3H), 4.17 (d, 1H, J=7.27 Hz), 3.39 (s, 3H), 3.38 (s, 3H), 3.1–2.9 (m, 3H), 2.75 (dd, 1H, J=9.28, 14.12 Hz), 2.53 (dd, 1H, J=5.47, 15.58 Hz), 2.33 (dd, 1H, J=7.96, 15.53 Hz), 2.04 (m, 1H), 1.88 (s, 3H), 1.8–1.2 (m, 6H), 1.41 (s, 9H), 0.94 (d, 6H, J=6.74 Hz).

Step B

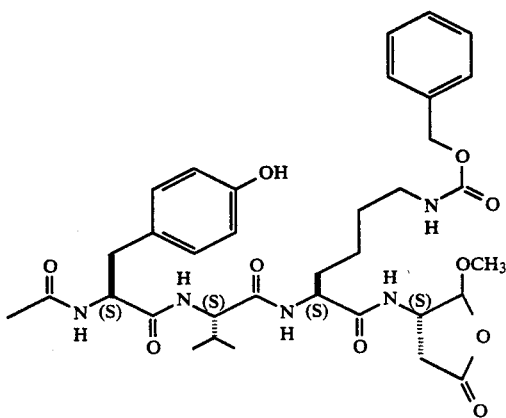

N-(N-Acetyl-tyrosinyl-valinyl-ε-CBZ-lysinyl)-3-amino-4-oxobutanoic acid. A solution of N-(N-Acetyl-tyrosinyl-valinyl-ε-CBZ-lysinyl)-3-amino-4-oxobutanoic acid β-tert-butyl ester dimethyl acetal (14.9 mg) was treated with 1 mL of trifluoroacetic acid, aged for 15 minutes, and concentrated in vacuo. The residue was dissolved in 1.0 mL of methanol and 1.0 mL of water containing 20 uL of thionyl chloride was added. After 1 hour, the pH of the solution was adjusted to around 5 with sodium acetate to afford a solution of the title compound: $^1$H NMR (200 MHz, CD$_3$OD) δ7.33 (br s, 5H), 7.05 (br d, 2H, J=8.35 Hz), 6.74 (br d, 2H, J=8.35 Hz), 4.6–3.9 (m, 5H), 3.1–2.3 (m, 6H), 1.98 (m, 1H), 1.92 (s, 3H), 1.8–1.2 (m, 6H), 0.89 (d, 6H, J=6.60 Hz).

EXAMPLE 8

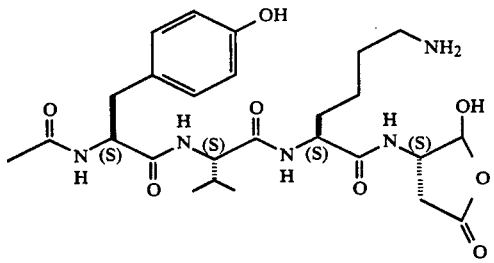

N-(N-Acetyl-tyrosinyl-valinyl-lysinyl)-3-amino-4-oxobutanoic acid. A solution of N-(N-Acetyl-tyrosinyl-valinyl-ε-CBZ-lysinyl)-3-amino-4-oxobutanoic acid β-tert-butyl ester dimethyl acetal (16.8 mg) was dissolved in 2 mL of methanol and 10 mg of Pearlman's catalyst (Pd(OH)$_2$ on Carbon) was added. After 30 minutes under hydrogen, the mixture was filtered and concentrated. The residue was treated with 2 mL of trifluoroacetic acid, aged for 15 minutes, and concentrated in vacuo. The product was dissolved in 1.0 mL of methanol and 1.0 μL of water containing 20 uL of thionyl chloride was added. After 1 hour, the pH of the solution was adjusted to around 5 with sodium acetate to afford a solution of the title compound: $^1$H NMR (200 MHz, CD$_3$OD) δ7.10 (br d, 2H, J=8.01 Hz), 6.77 (br d, 2H, J=8.25 Hz), 4.7–4.0 (m, 5H), 3.1–2.4 (m, 6H), 2.04 (m, 1H), 1.95 (s, 3H), 1.9–1.3 (m, 6H), 0.90 (d, 6H, J=6.59 Hz).

EXAMPLE 9

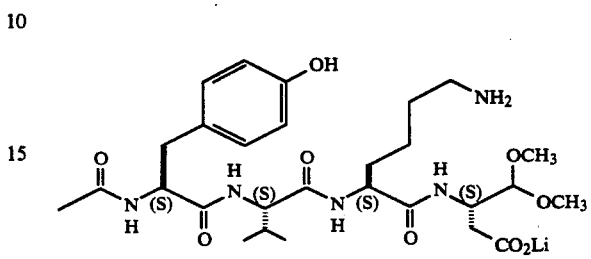

N-(N-Acetyl-tyrosinyl-valinyl-lysinyl)-3-amino-4-oxobutanoic acid dimethyl acetal. A solution of N-(N-Acetyl-tyrosinyl-valinyl-ε-CBZ-lysinyl)-3-amino-4-oxobutanoic acid β-tert-butyl ester dimethyl acetal (15.6 mg) was disolved in 2 mL of methanol and 10 mg of Pearlman's catalyst (Pd(OH)$_2$ on Carbon) was added. After 30 min under hydrogen, the mixture was filtered and concentrated. The solid was disolved in 1 mL of methanol and 1 mL of water. Lithium hydroxide hydrate (22 mg) was added. After 16 hours at ambient temperature, the mixture was concentrated in vacuo to give the title compound in the presence of lithium hydroxide: $^1$H NMR (200 MHz, CD$_3$OD) δ6.88 (br d, 2H, J=8.4 Hz), 6.54 (br d, 2H, J=8.4 Hz), 4.6–4.1 (m, 5H), 3.38 (s, 6H), 3.0–2.2 (m, 6H), 2.08 (m, 1H), 1.88 (s, 3H), 1.9–1.2 (m, 6H), 0.94 (d, 6H, J=6.7 Hz), 0.91 (d, 3H, J=6.7 Hz).

What is claimed is:

1. A method of purifying interleukin-1b converting enzyme comprising in sequential order:
   (a) loading a preparation containing interleukin-1β converting enzyme onto a affinity chromatography matrix,
   said matrix consisting essentially of epoxy-activated cross-linked dextran, and a compound of formula I

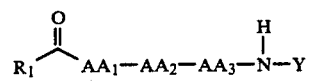

co-valently bound to the epoxy portion of said epoxy-activated crosslinked dextran, wherein Y is:

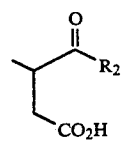

AA$_1$ is an amino acid of formula AI

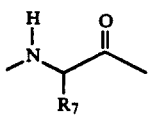

AA$_2$ is an amino acid of formula AII

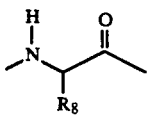

AA$_3$, is an amino acid of formula AIII

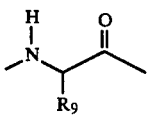

R$_1$ is methyl;
R$_2$ is hydrogen;
R$_7$ is phenylC$_{1-6}$alkyl;
R$_8$ is C$_{1-6}$alkyl; and
R$_9$ is substituted C$_{1-6}$ alkyl
wherein the substituent is
 (a) H,
 (b) OH,
 (c) CO$_2$H,
 (d) NH$_2$,
 (e) formyl,
 (f) oxiranyl,
 (g) halo,
 (h) thiol,
 (i) substituted phenyl C$_{1-6}$alkyl, wherein the substituent is hydroxy, amino, or carboxy, formyl, oxiranyl, thiol, hydroxy C$_{1-6}$ alkyl, amino C$_{1-6}$ alkyl, carboxy C$_{1-6}$ alkyl, formyl C$_{1-6}$ alkyl, oxiranyl C$_{1-6}$ alkyl, thiol C$_{1-6}$ alkyl, halo C$_{1-6}$ alkyl;
 (b) washing said matrix with a buffer having a pH of 6.5 to 7.5 to remove contaminating proteins;
 (c) eluting said interleukin-1β converting enzyme by addition of a solution of an independently selected compound of Formula I in said buffer, and
 (d) recovering said interleukin-1β converting enzyme.

2. A method of purifying interleukin-1b converting enzyme comprising in sequential order:
 (a) loading a preparation containing interleukin-1β converting enzyme onto a affinity chromatography matrix,
 said matrix consisting essentially of epoxy-activated cross-linked dextran, and a compound selected from the group consisting of
  N-(N-Acetyl-tyrosinyl-valinyl-lysinyl)-3-amino-4-oxobutanoic acid;
  N-(N-Acetyl-tyrosinyl-valinyl-alaninyl)-3-amino-4-oxobutanoic acid; and
  N-(N-Acetyl-tyrosinyl-valinyl-(ε-CBZ-lysinyl))-3-amino-4-oxobutanoic acid;
 co-valently bound to the epoxy portion of said epoxy-activated crosslinked dextran;
 (b) washing said matrix with a buffer having a pH of 6.5 to 7.5 to remove contaminating proteins;
 (c) eluting said interleukin-1β converting enzyme by addition of a compound selected from the group consisting of
  N-(N-Acetyl-tyrosinyl-valinyl-lysinyl)-3-amino-4-oxobutanoic acid;
  N-(N-Acetyl-tyrosinyl-valinyl-alaninyl)-3-amino-4-oxobutanoic acid; and
  N-(N-Acetyl-tyrosinyl-valinyl-(ε-CBZ-lysinyl))-3-amino-4-oxobutanoic acid in said buffer; and
 (d) recovering said interleukin-1β converting enzyme.

* * * * *